US00PP30845P3

(12) United States Plant Patent
Kordes

(10) Patent No.: US PP30,845 P3
(45) Date of Patent: Aug. 27, 2019

(54) MINIATURE ROSE PLANT NAMED 'KORPOT080'

(50) Latin Name: *Rosa hybrida*
Varietal Denomination: KORpot080

(71) Applicant: W. KORDES' SÖHNE Rosenschulen GmbH & Co KG, Klein Offenseth-Sparrieshoop (DE)

(72) Inventor: Wilhelm-Alexander Kordes, Klein Offenseth-Sparrieshoop (DE)

(73) Assignee: W. KORDES SÖHNE Rosenschulen GmbH & Co KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 15/732,566

(22) Filed: Nov. 29, 2017

(65) Prior Publication Data

US 2019/0166740 P1 May 30, 2019

(30) Foreign Application Priority Data

Sep. 20, 2017 (QZ) ..... PBR 20172297

(51) Int. Cl.
*A01H 5/02* (2018.01)
*A01H 6/74* (2018.01)

(52) U.S. Cl.
USPC ..... Plt./118
CPC ..... *A01H 6/749* (2018.05)

(58) Field of Classification Search
USPC ..... Plt./118
CPC ..... A01H 6/749; A01H 5/02
See application file for complete search history.

(56) References Cited

U.S. PATENT DOCUMENTS

PP19,638 P2 1/2009 Kordes

*Primary Examiner* — Keith O. Robinson
(74) *Attorney, Agent, or Firm* — Buchanan Ingersoll & Rooney PC

(57) ABSTRACT

A new and distinct variety of Miniature Rose Plant, herein referred to by its cultivar name, 'KORpot080', is provided which forms in abundance on a substantially continuous basis attractive, dark yellow colored blossoms. The vegetation is vigorous and the growth habit is compact. Attractive ornamental foliage is formed with good disease resistance. The new variety is particularly well suited for providing distinctive ornamentation in the landscape.

1 Drawing Sheet

Botanical/commercial classification: Latin name—*Rosa hybrida.* Common name—Miniature Rose Plant.
Varietal denomination—'KORpot080'.

CROSS-REFERENCE TO RELATED APPLICATIONS

This application claims priority to Plant Breeders' Rights Application Number 2017/2297 which was filed in European Union through Community Plant Variety Office on Sep. 20, 2017, of which the content of is hereby expressly incorporated by reference in its entirety for all purposes.

SUMMARY OF THE INVENTION

The new variety of *Rosa hybrida* Miniature Rose Plant of the present invention was created during 2013 at Offenseth-Sparrieshoop, Germany by artificial pollination wherein two parents were crossed which previously had been studied in the hope that they would contribute the desired characteristics. The female parent (i.e., seed parent) of the new variety was an unnamed seedling from a previous cross of an unnamed seedling and 'KORpedia' (U.S. Plant Pat. No. 19,638). The male parent (i.e., pollen parent) of the new variety was an unnamed seedling.

The parentage can be summarized as follows:

(unnamed seedling x 'KORpedia') x unnamed seedling

The seeds resulting from the above pollination were sown and small plants were obtained which were physically and biologically different from each other. Selective study resulted in the identification of a single plant of the new variety.

It was found that the new Miniature Rose Plant of the present invention possesses the following combination of characteristics:

(a) abundantly and substantially continuously forms attractive, dark yellow colored blossoms, (b) exhibits a compact growth habit, (c) forms vigorous vegetation, and (d) forms attractive ornamental foliage with good disease resistance.

The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from its ancestors. More specifically, the seed parent (unnamed seedling x 'KORpedia') exhibits a lighter yellow flower color than the new variety and the new variety has an improved shelf life and mildew resistance compared to the seed parent. Additionally, the unnamed seedling male parent variety (i.e., pollen parent) exhibits a lower petal count and a less upright growth habit compared to the new variety, as the pollen parent displays a moderately spreading growth habit, whereas the new variety displays a compact growth habit. Moreover, new variety can be readily distinguished from other similar non-parental varieties. For example, the 'KORpot045' variety (U.S. Plant Pat. No. 27,186) displays flowers with a lower petal count and larger diameter compared to the new variety. In addition the 'KORpot045' variety exhibits flower which fade more quickly than the new variety and the 'KORpot045' variety has a lower shelf life than the new variety.

The new variety has been found to undergo asexual propagation in Klein Offenseth-Sparrieshoop, Germany by a number of routes such as vegetative cuttings. Asexual propagation techniques in Germany have shown that the characteristics of the new variety are homogeneous, stable, and strictly transmissible by such asexual propagation from one generation to another. Accordingly, the new variety undergoes asexual propagation in a true-to-type manner.

The new variety has been named 'KORpot080'.

BRIEF DESCRIPTION OF THE PHOTOGRAPHS

The accompanying photograph shows, as nearly true as it is reasonably possible to make the same in color illustrations of this character, a typical specimen of the new variety. The illustrated rose plant of the new variety was approximately twelve weeks of age and was observed at Klein Offenseth-Sparrieshoop, Germany while growing indoors on its own roots in a 10.5 cm container.

FIG. 1—illustrates a specimen of a plant displaying floral buds and flowers at varying points of opening.

DETAILED BOTANICAL DESCRIPTION

The chart used in the identification of colors is that of The Royal Horticultural Society (R.H.S. Colour Chart, 2015 Edition). The terminology which precedes reference to the chart has been added to indicate the corresponding color in more common terms. The description is based on a one-year old specimen of the new variety, observed during July, while growing in a one-gallon container on its own roots in a greenhouse in Cochranville, Pa., U.S.A.

Class: Miniature Rose Plant.

Plant:

*Habit.*—Compact, very bushy and upright.

*Height.*—Approximately 26.0 cm on average.

*Width.*—Approximately 30.0 cm on average.

*Growth.*—Moderate.

Branches:

*Stem color.*—Commonly near Yellow-Green Group 144A on both young and older wood.

*Stem length.*—Main stems: approximately 25.0 cm on average. Secondary stems: approximately 5.0 cm on average.

*Stem texture.*—Young wood and old wood are glabrous.

*Thorns.*—Young thorns: moderate amount; length is approximately 4.0 mm on average, width is approximately 1.0 mm at point of attachment on average, and color is commonly near Greyed-Red Group 178B. Old thorns: moderate amount; length is approximately 5.0 mm on average, width is approximately 1.0 mm at point of attachment on average, and color is commonly near Greyed-Orange Group 176B.

Foliage:

*General appearance.*—Ornamental with good disease resistance.

*Young foliage.*—Upper surface color: commonly near Greyed-Purple Group 183A. Under surface color: commonly near Greyed-Purple Group 183B.

*Old foliage.*—Upper surface color: commonly near Green Group NN137A. Under surface color: commonly near Green Group 138B.

*Petioles.*—Upper surface: texture is smooth, color is commonly near Green Group 137A. Under surface: texture is mostly smooth with sparse prickles, color is commonly near Yellow-Green Group 144A. Width: approximately 1.0 mm on average. Length: approximately 1.7 cm on average.

*Rachis.*—Color: upper surface is commonly between Brown Group 200C and Green Group 137A, under surface is commonly near Yellow-Green Group 144A.

*Stipules.*—Length: approximately 4.5 cm on average. Width: approximately 6.0 mm on average. Margin: entire to erose. Shape: apex is apiculate and base is flat. Color: upper surface is commonly near Yellow-Green Group 144C; lower surface is commonly near Yellow-Green Group 144B.

*Leaf margin.*—Serrate.

*Glossiness of upper-side of leaf.*—Medium.

Leaflets:

*Number.*—3, 5, and 7.

*Shape.*—Ovate; apex is acute; and base is cuneate.

*Venation.*—Pattern is reticulate.

*Texture.*—Upper surface is smooth; under surface is smooth.

*Size.*—Terminal leaflet: length is approximately 3.5 cm on average and width is approximately 2.5 cm on average. Lower leaflets: length is approximately 2.2 cm on average and width is approximately 1.2 cm on average. 5-Leaflet leaf: length is approximately 8.5 cm on average and width is approximately 6.5 cm on average.

Inflorescence:

*Number of flowers.*—Approximately 7 blooms on average on a plant at once.

*Number of blooms per stem or in a cluster.*—Commonly 1 bloom per stem on average.

*Peduncle.*—Color: commonly Yellow-Green Group 144A. Diameter: approximately 3.0 mm on average. Length: approximately 4.5 cm on average. Surface texture: glabrous. Strength: strong.

*Sepals.*—Number: commonly 5. Upper surface color and texture: covered in short pubescence and color is commonly near Yellow-Green Group 144A. Under surface color and texture: puberulent and color is commonly near Yellow-Green Group 144A. Size: length is approximately 1.9 cm on average and width is approximately 4.0 mm on average. Shape: lanceolate; apex is aristate; base is truncate, or flat at union with receptacle. Margin: entire with occasional extensions on two or three sepals measuring approximately 7.0 mm in length and approximately 3.0 mm in width.

*Bud.*—Shape: globular. Size: length is approximately 1.5 cm on average; width is approximately 1.5 cm on average. Color (when opening): commonly a blend of near Orange-Red Group 34C and near Yellow Group 11A.

*Flower.*—Dark yellow colored. Form: double, cuplike. Profile: flat. Diameter: approximately 3.5 cm on average. Height: approximately 3.0 cm on average. Duration: commonly on the plant approximately 15 days.

*Fragrance.*—None noticeable.

*Petal.*—Number: approximately 42 on average. Drop: good. Inner petals size: length is approximately 1.3 cm on average and width is approximately 1.2 cm on average. Outer petals size: length is approximately 2.0 cm on average and width is approximately 2.3 cm on average. Shape: overall shape is broadly obovate; apex shape is round; and base shape is cuneate. Margin: entire. Texture: upper surface is glabrous and lower surface is glabrous. Upper surface color: commonly near Yellow Group 12A, some with near Orange-Red Group 33A on the very edge of the margin apex. Under surface color: commonly near Yellow Group 12B, with some of the outermost petals exhibiting splotching of near Orange-Red Group 33A. Basal spot: absent.

*Petaloids.*—Number: approximately 3-5 per flower on average. Upper surface color: commonly near Yellow-Orange Group 14A. Under surface color: commonly near Yellow-Orange Group 14B. Texture: smooth. Size: length is approximately 1.4 cm on average and width is approximately 6.0 mm on average. Margins: variable, entire to erose. Shape: overall shape is variable, oblong and mostly curving inward; apex is round, and base is cuneate.

*Stamen.*—Number: approximately 80 on average. Anthers: number is about 80 and color is commonly near Greyed-Orange Group 163B; length is approximately 3.0 mm on average; and shape is oval. Filaments: length is approximately 4.0 mm on average and color is commonly near Greyed-Orange Group 163C.

*Pistils.*—Arrangement: separate and free. Number: approximately 70 on average. Length: approximately 1.0 cm. Style: color is commonly near Orange-White Group 159D and some exhibiting a small hint of near Red Group 50B at the base of the stigma; and length is commonly less than 1.0 mm. Stigma: color is commonly near Greyed-Yellow Group 162B; diameter is commonly less than 1.0 mm on average; length is commonly less than 1.0 mm; shape is flat to disc shaped. Ovary: length is commonly near 1.5 mm on average, width is commonly less than 1.0 mm on average, and color is commonly near Greyed-Yellow Group 160D.

*Receptacle.*—Achenes stand on the bottom and wall; diameter is approximately 4.0 mm on average, length is approximately 6.0 mm on average, shape is round, color is commonly near Yellow-Green Group 144A, and surface texture is smooth.

*Pollen.*—None observed.

*Hips/seed.*—None observed.

Development:

*Resistance to disease.*—Good resistance has been observed in regards to *Sphaerotheca pannosa* and *Botrytis* (*Botrytis cinerea*) disease under normal greenhouse growing conditions in Cochranville, Pa.

*Vegetation.*—Dark green, vigorous and strong.

*Blooming.*—Abundant and substantially continuous.

*Hardiness.*—Unknown.

Plants of the 'KORpot080' variety have not been observed under all possible environmental conditions to date. Accordingly, it is possible that the phenotypic expression may vary somewhat with changes in light intensity and duration, cultural practices, and other environmental conditions.

I claim:

1. A new and distinct Miniature Rose Plant characterized by the following combination of characteristics:

(a) abundantly and substantially continuously forms attractive, dark yellow colored blossoms, (b) exhibits a compact growth habit, (c) forms vigorous vegetation, and (d) forms attractive ornamental foliage with good disease resistance;

substantially as herein shown and described.

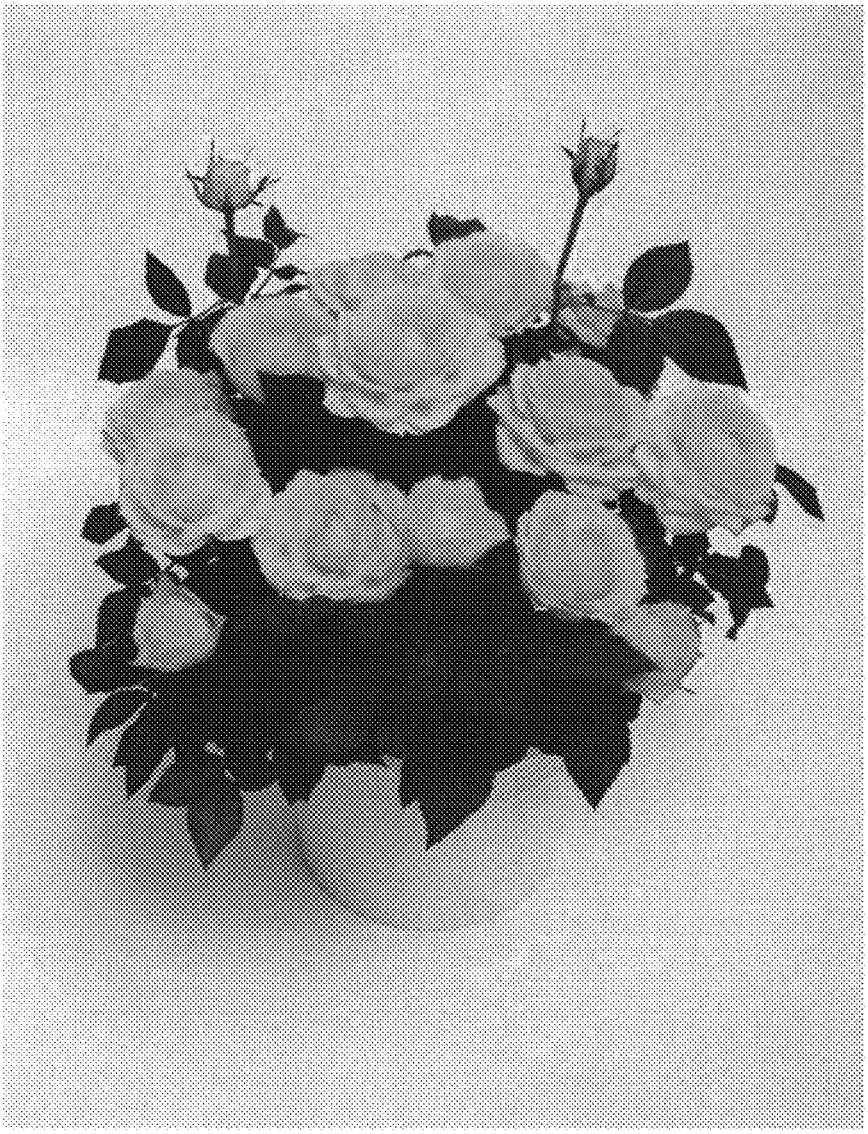

* * * * *